US010349972B2

(12) United States Patent
Bar-Cohen et al.

(10) Patent No.: US 10,349,972 B2
(45) Date of Patent: Jul. 16, 2019

(54) PLACID WIRE MECHANISM OF PENETRATING BLOCKINGS AND OCCLUSIONS IN ARTERIES

(71) Applicants: CALIFORNIA INSTITUTE OF TECHNOLOGY, Pasadena, CA (US); PLACIDUS LLC, Falls Church, VA (US)

(72) Inventors: Yoseph Bar-Cohen, Pasadena, CA (US); Stewart Sherrit, Pasadena, CA (US); Hyeong Jae Lee, Pasadena, CA (US); Mircea Badescu, Pasadena, CA (US); Xiaoqi Bao, Pasadena, CA (US); Yoseph Shalev, Falls Church, VA (US); Joshua Leavitt, Falls Church, VA (US)

(73) Assignees: CALIFORNIA INSTITUTE OF TECHNOLOGY, Pasadena, CA (US); PLACIDUS LLC, Falls Church, VA (US)

( * ) Notice: Subject to any disclaimer, the term of this patent is extended or adjusted under 35 U.S.C. 154(b) by 388 days.

(21) Appl. No.: 15/218,979

(22) Filed: Jul. 25, 2016

(65) Prior Publication Data
US 2017/0252058 A1    Sep. 7, 2017

Related U.S. Application Data

(60) Provisional application No. 62/303,989, filed on Mar. 4, 2016.

(51) Int. Cl.
*A61B 17/22* (2006.01)
*A61D 1/02* (2006.01)
(Continued)

(52) U.S. Cl.
CPC .. *A61B 17/32075* (2013.01); *A61B 17/22012* (2013.01); *A61B 17/320068* (2013.01); *A61B 2017/00402* (2013.01); *A61B 2017/22015* (2013.01); *A61B 2017/22079* (2013.01); *A61B 2017/22094* (2013.01); *A61B 2017/32007* (2017.08); *A61B 2017/32008* (2013.01); *A61B 2017/320098* (2017.08)

(58) Field of Classification Search
None
See application file for complete search history.

(56) References Cited

U.S. PATENT DOCUMENTS 5,713,848 A * 2/1998 Dubrul ............... A61B 17/22
 601/2
5,906,623 A * 5/1999 Peterson .......... A61B 17/22012
 604/22

(Continued)

OTHER PUBLICATIONS

International Search Report and Written Opinion for International application No. PCT/US2016/043908 dated Nov. 21, 2016. (19 pages).

(Continued)

*Primary Examiner* — Amy R Weisberg
(74) *Attorney, Agent, or Firm* — Steinfl + Bruno, LLP

(57) ABSTRACT

An arterial blockage percussive drill having a guiding sleeve, a drilling wire slidably coupled to the guiding sleeve and a percussive actuator coupled to the drilling wire to longitudinally oscillate the drilling wire into an arterial blockage.

14 Claims, 24 Drawing Sheets

(51) Int. Cl.
*A61B 17/3207* (2006.01)
*A61B 17/32* (2006.01)
*A61B 17/00* (2006.01)

(56) References Cited

U.S. PATENT DOCUMENTS

| | | | | |
|---|---|---|---|---|
| 5,971,949 | A * | 10/1999 | Levin | A61B 17/22012 604/22 |
| 6,551,337 | B1 * | 4/2003 | Rabiner | A61B 17/22012 606/169 |
| 6,863,136 | B2 | 3/2005 | Bar-Cohen et al. | |
| 8,657,027 | B2 * | 2/2014 | Sherrit | B23B 37/00 173/2 |
| 8,958,270 | B2 | 2/2015 | Sherrit et al. | |
| 2002/0077643 | A1 * | 6/2002 | Rabiner | A61B 17/22012 606/169 |
| 2002/0107446 | A1 * | 8/2002 | Rabiner | A61B 17/22012 600/439 |
| 2002/0168611 | A1 * | 11/2002 | Kim | A61C 3/03 433/119 |
| 2003/0099917 | A1 * | 5/2003 | Wietecha | A61C 3/03 433/119 |
| 2003/0157458 | A1 * | 8/2003 | Buchanan | A61C 1/07 433/166 |
| 2003/0181812 | A1 * | 9/2003 | Rabiner | A61B 17/22012 600/439 |
| 2004/0097996 | A1 * | 5/2004 | Rabiner | A61B 17/22012 606/159 |
| 2004/0127925 | A1 * | 7/2004 | Du | A61B 17/22012 606/167 |
| 2004/0147945 | A1 * | 7/2004 | Fritzsch | A61B 17/320016 606/169 |
| 2006/0184186 | A1 * | 8/2006 | Noone | A61B 17/32002 606/159 |
| 2007/0193757 | A1 * | 8/2007 | Bar-Cohen | B25D 11/064 173/90 |
| 2008/0281253 | A1 * | 11/2008 | Injev | A61F 9/00745 604/22 |
| 2008/0306499 | A1 * | 12/2008 | Katoh | A61B 17/22 606/159 |
| 2009/0069712 | A1 * | 3/2009 | Mulvihill | A61B 10/025 600/564 |
| 2009/0270888 | A1 * | 10/2009 | Patel | A61B 17/320758 606/159 |
| 2010/0174233 | A1 * | 7/2010 | Kuban | A61M 25/09033 604/95.01 |
| 2010/0204613 | A1 * | 8/2010 | Rollins | A61M 25/09041 600/585 |
| 2011/0208222 | A1 * | 8/2011 | Ljahnicky | A61B 17/320758 606/159 |
| 2012/0037390 | A1 * | 2/2012 | Bao | B23B 37/00 173/113 |
| 2012/0209303 | A1 * | 8/2012 | Frankhouser | A61B 10/025 606/169 |
| 2014/0107683 | A1 * | 4/2014 | Kuhner | B05B 3/14 606/169 |
| 2014/0249472 | A1 * | 9/2014 | Mulvihill | A61B 25/00 604/95.01 |
| 2015/0351644 | A1 * | 12/2015 | Lee | A61B 5/6851 600/486 |
| 2016/0038165 | A1 * | 2/2016 | Cook | A61B 17/22012 606/128 |
| 2016/0128769 | A1 * | 5/2016 | Rontal | A61B 18/1492 600/104 |
| 2016/0346519 | A1 * | 12/2016 | Bagwell | A61B 10/025 |
| 2018/0185052 | A1 * | 7/2018 | Zhou | A61B 17/32002 |

OTHER PUBLICATIONS

Bar-Cohen, Y., et al. "Ultrasonic/Sonic Driller/Corer (USDC) with Integrated Sensors," NTR, Aug. 30, 1999, Item No. 0448h, Docket No. 20856, (Nov. 17, 1999). NASA Tech Briefs, vol. 25, No. 1, Jan. 2001, pp. 38-39.

Sherrit, S., et al. "Miniature Low-Mass Drill Actuated by Flextensional Piezo Stack", NTR Docket No. 45857, NASA Tech Briefs, vol. 34, No. 8, Aug. 2010, pp. 6-7.

* cited by examiner

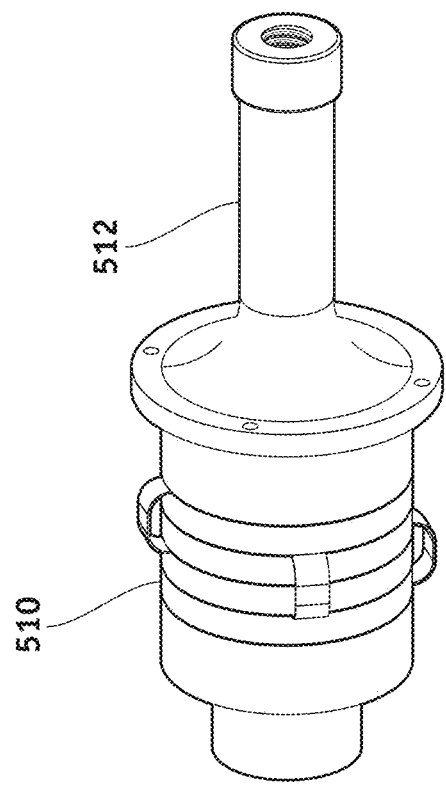
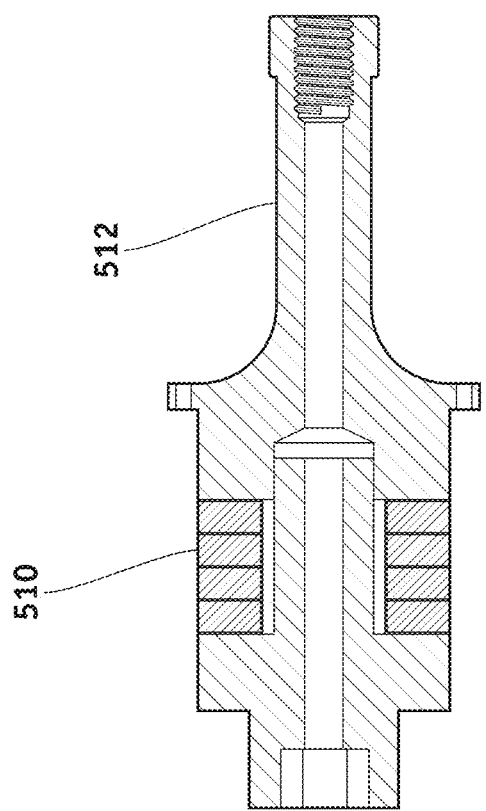
FIG. 5

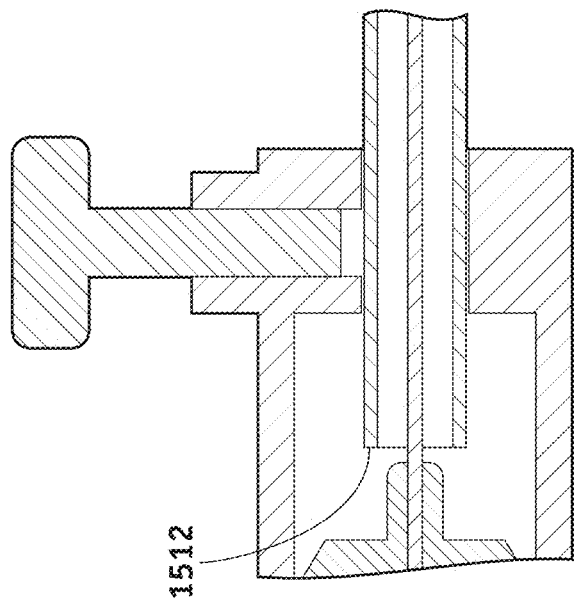
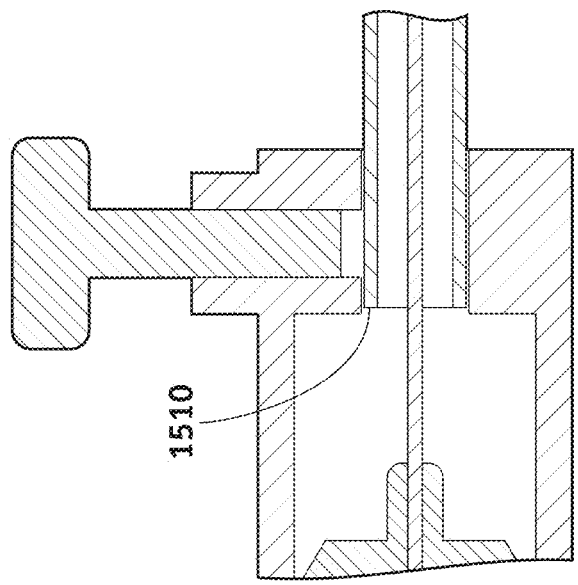
FIG. 15

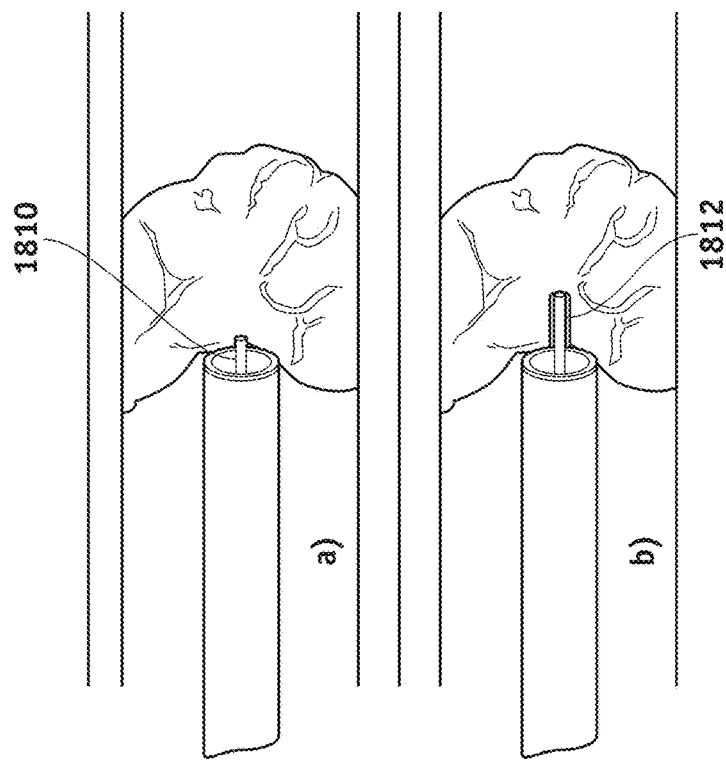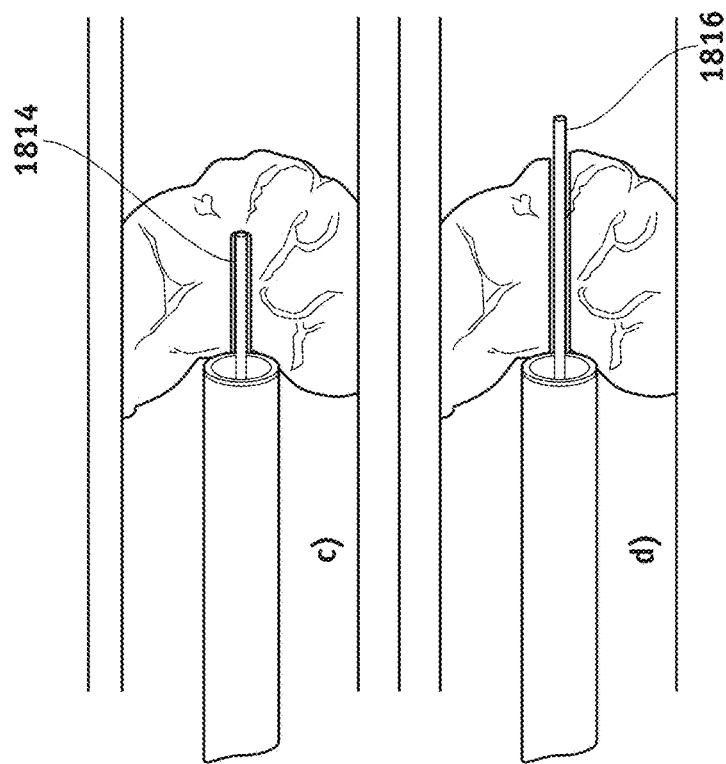
FIG. 18

US 10,349,972 B2

PLACID WIRE MECHANISM OF PENETRATING BLOCKINGS AND OCCLUSIONS IN ARTERIES

CROSS REFERENCE TO RELATED APPLICATIONS

The present application claims priority to U.S. Provisional Patent Application 62/303,989 filed on Mar. 4, 2016, entitled Placid-Wire-Mechanism of Penetrating Blocking/Occlusion in Arteries, the disclosure of which is incorporated herein by reference in its entirety. The instant application incorporates by reference the following in their entirety: PCT Patent application number PCT/US01/14289, entitled "Smart-ultrasonic/sonic driller/corer", published Jan. 15, 2004; U.S. Pat. No. 6,863,136, entitled "Smart-ultrasonic/sonic driller/corer", granted Mar. 8, 2005; U.S. Pat. No. 8,657,027, entitled "Single Piezo-Actuator Rotary-Hammering (SPaRH) Drill", granted Feb. 25, 2014; and U.S. Pat. No. 8,958,270, entitled "Monolithic Flexure Pre-stressed Ultrasonic Horns", granted Feb. 17, 2015.

FEDERALLY SPONSORED RESEARCH OR DEVELOPMENT

The invention described herein was made in the performance of work under a NASA contract NNN12AA01C, and is subject to the provisions of Public Law 96-517 (35 USC 202) in which the Contractor has elected to retain title.

TECHNOLOGY

The present disclosure relates generally to wire drills. More particularly, an embodiment of the present disclosure relates to percussion actuated wire drills.

BRIEF DESCRIPTION OF THE DRAWINGS

An embodiment of the instant disclosure is illustrated by way of example, and not in way by limitation, in the figures of the accompanying drawings and in which like reference numerals refer to similar elements and in which:

FIG. 5 depicts an example piezo transducer and stepped dog-bone horn in accordance with an embodiment of the disclosure;

FIG. 15 depicts an example coarse length adjuster in accordance with an embodiment of the disclosure;

FIG. 18 panels a), b) c) and d) depict an example drilling wire in use in accordance with an embodiment of the disclosure;

SUMMARY

Figure 1:
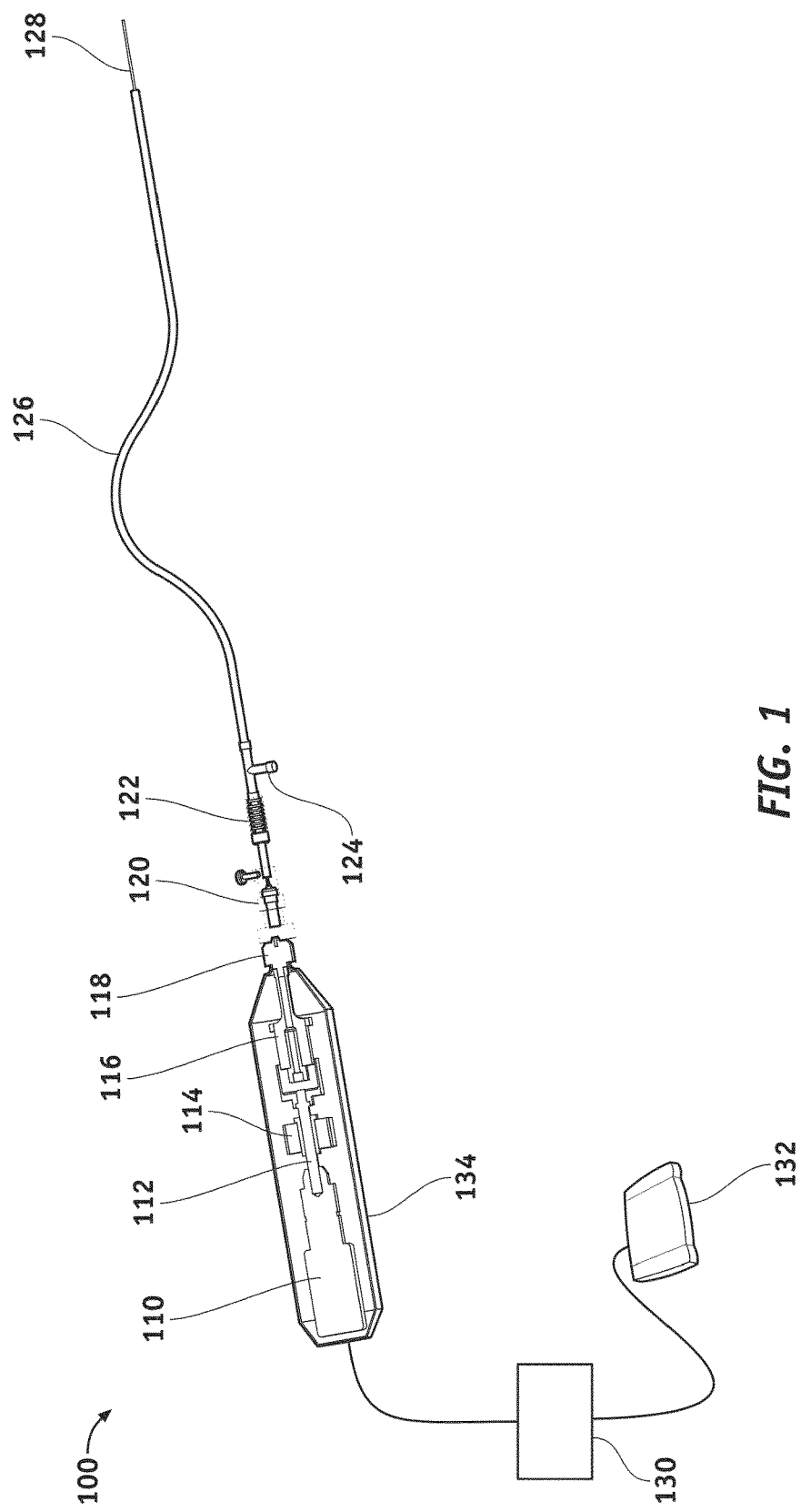
FIG. 1 depicts an example overview of a handheld arterial blockage drill in accordance with an embodiment of the disclosure.

In a first aspect of the disclosure, an arterial blockage percussive drill that comprises a guiding sleeve, a drilling wire slidably coupled to the guiding sleeve and a percussive actuator coupled to the drilling wire to longitudinally oscillate the drilling wire into an arterial blockage.

In a second aspect of the disclosure, an arterial blockage percussive drill that comprises a drilling wire slidably coupled to the guiding sleeve, a percussive actuator coupled to the drilling wire to longitudinally oscillate the drilling wire into an arterial blockage and a rotary actuator coupled to the drilling wire to rotate the drilling wire while the drilling wire is longitudinally oscillating.

In a third aspect of the disclosure, an arterial blockage percussive drill that comprises a drilling wire slidably coupled to the guiding sleeve and a helical oscillator coupled to the drilling wire to longitudinally and rotationally oscillate the drilling wire into an arterial blockage.

In a fourth aspect of the disclosure, an arterial blockage percussive drill that comprises a vented guiding sleeve, a drilling wire slidably coupled to the vented guiding sleeve, a percussive actuator coupled to the drilling wire to longitudinally oscillate the drilling wire into an arterial blockage, a perforated disk debris crusher coupled to the drilling wire to crush debris drilled out by the drilling wire and oscillated by the percussive actuator and a perforated disk debris filter coupled to the drilling wire to filter crushed debris and pass efflux to vents in the vented guiding sleeve.

Definitions

A drilling wire is a semi-rigid wire that is used for drilling an arterial occlusion. The wire is coupled to an actuator at a connector end and contacts the occlusion for its drilling at a bit end. The semi-rigid wire may be metallic, plastic, fiber, composite, flexible glass and the like.

A guiding element is a cone, ball, or other solid element that is mounted near the bit of the drilling wire. The element has a diameter that is larger than the drilling wire and it is used to center the drilling wire within the artery to minimize potential damage to the artery wall.

A guiding sleeve is a sleeve within which the drilling wire is inserted and is used as a guide for the drilling wire. The guiding sleeve may also serve as a conduit for delivering fluids such as medications or cooling saline.

A guide wire is the combination of a guiding sleeve with the inserted drilling wire.

An artery blockage drilling system is a vibrational mechanism, such as a piezoelectric driven actuator that delivers percussive action to the drilling wire. The percussive action may be augmented by rotation.

System Description

Peripheral vascular diseases (PVDs) are circulation disorders that affect veins and arteries. PVD may result from atherosclerosis inflammatory processes that lead to the formation of stenosis, embolism, or thrombus, and in time may create chronic total occlusions, which may cause either acute or chronic ischemia, i.e. lack of blood supply. When the blockage severity reaches chronic total occlusion it may have serious effects including physical disabilities and increased probability of mortality. PVD that develops only in the arteries is referred to as peripheral arterial disease (PAD) and peripheral artery occlusive disease (PAOD) approximately 12 to 20 percent of the population over age 65 have PAD.

The capability to drill through an occlusion may provide a path for other medical means of expanding and possibly removing the remainder of an occlusion. Restoring blood flow beyond a total occlusion may prevent amputation or result in saving a life. The arterial blockage percussive drill may be used on any partial or total occlusion in a vein or artery.

The arterial blockage percussive drill described in this disclosure employs percussive vibrations generated by piezoelectric actuators to drive a drilling wire enclosed in a guiding sleeve through an arterial obstruction. The device acts as an occlusion drill for treating diseased arteries. The drill may minimize potential thermal or physical damage to artery walls and may produce minute size fragments.

A percussive actuator drives a drilling wire that is inserted into a vein or artery via a guiding sleeve. The drilling wire is used to penetrate plaque as part of the procedure of treating plagued arteries.

A portable configuration of the arterial blockage percussive drill allows the surgeon to manipulate the guiding sleeve and the drilling wire while holding the device. This option is shown in FIGS. 1 and 2.

Illustration of a handheld arterial blockage percussive drill 100 comprising combined vibration and rotation actuators and the drilling wire within a guiding sleeve is shown in FIG. 1. In this embodiment a rotary actuator 110 is coupled by an actuator coupling 112 and slip ring 114 to an actuator coupler which is coupled to a percussive actuator 116 having a motion transfer horn and coupled to a chuck 118. A coarse length adjuster 120 and fine length adjuster 122 are coupled to the guiding sleeve. A fluid access port 124 allows fluids to be routed between the guiding sleeve 126 and the drilling wire 128. The percussive actuator and the rotary actuator are controlled by a control box 130 and a foot pedal switch 132. The portable body of the drill 134 contains the actuation components of the drill.

Rotation of the drilling wire is an option which may increase the efficiency of the arterial blockage percussive drill in terms of fracturing plaques and steering the drilling wire away from the wall of an artery. The wire may be rotated in one direction, stopped after a predetermined rotation such as 45, 90 or 180 degrees or the like, and either rotated back a predetermined rotation or rotated forward. The wire may also be oscillated continuously through a predetermined rotation angle. The rotary actuator may rotate the drilling wire through a predetermined first rotational angle in a first direction, e.g. 45 degrees clockwise, and rotates through a predetermined second rotational angle, e.g. 45 or 90 degrees, in at least one of the first direction (for example clockwise) or a second direction (for example counter clockwise) counter to the first direction. The predetermined first angle and second angle may be roughly equivalent or different.

Figure 2:
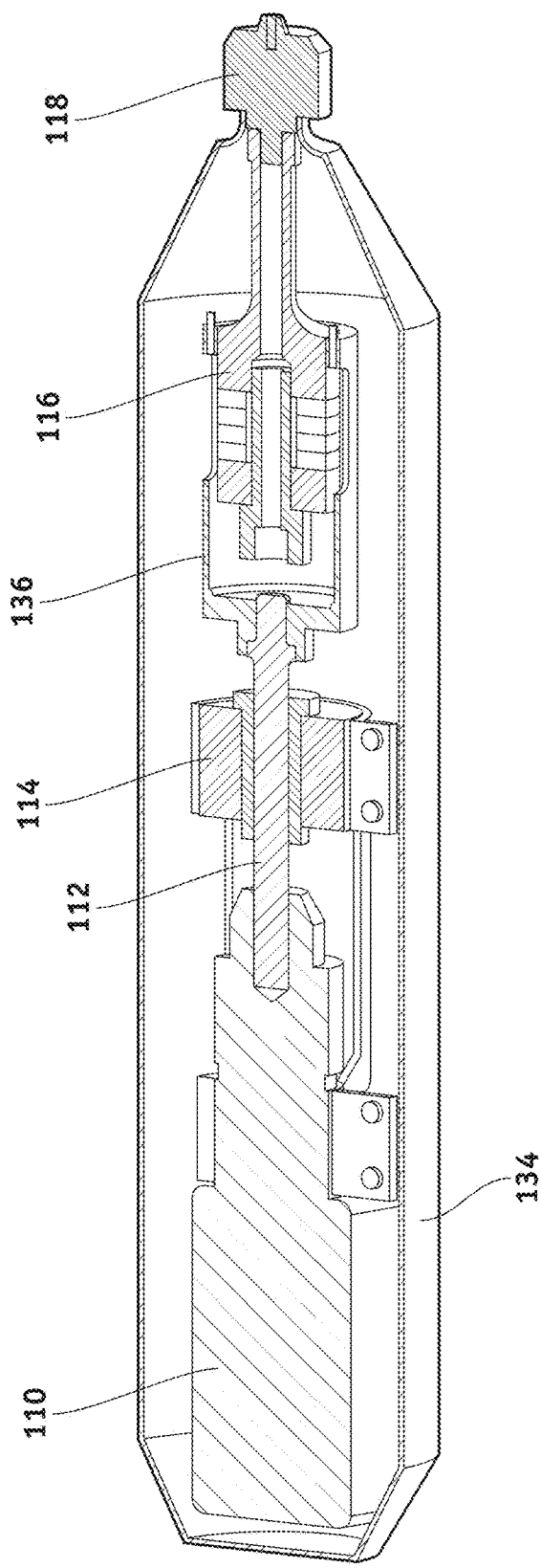
FIG. 2 depicts an example handheld actuator assembly of the arterial blockage drill in accordance with an embodiment of the disclosure.

FIG. 2 depicts details of an embodiment of the actuation mechanism. The rotary actuator 110, is coupled to an actuator coupling 112 with a slip ring 114 coupled to the actuator coupling. The rotary actuator imparts a turning action to a drilling wire which may increase the efficiency of drilling. The rotary actuator may be direct current (DC) brush or brushless, alternating current (AC) induction, synchronous, linear, or digital stepper actuator or the like. The rotary actuator may oscillate, rotate in one direction and stop before rotation again or may continuously rotate and the like. The actuator coupling 112 is coupled to an actuator coupling 136 which in turn is coupled to the percussive actuator 116 which imparts the percussive motion to the drilling wire to pulverize the occlusive material. The percussive actuator comprises a stacked piezoelectric element coupled to a motion transfer horn to provide compressive stress to the piezoelectric element and to transfer the motion from the piezoelectric element to a drilling wire coupler such as chuck 118. The drilling wire coupler may provide either a removable coupling or a permanent coupling to the drilling wire.

FIG. 2 depicts the drill with rotation capability. The coupling of the drilling wire to the motion transfer horn may be through a direct coupling, i.e. coupling the wire via brazing or other seaming method, or may be through the use of a chuck which allows the drilling wire to be released for replacement.

Figure 3:
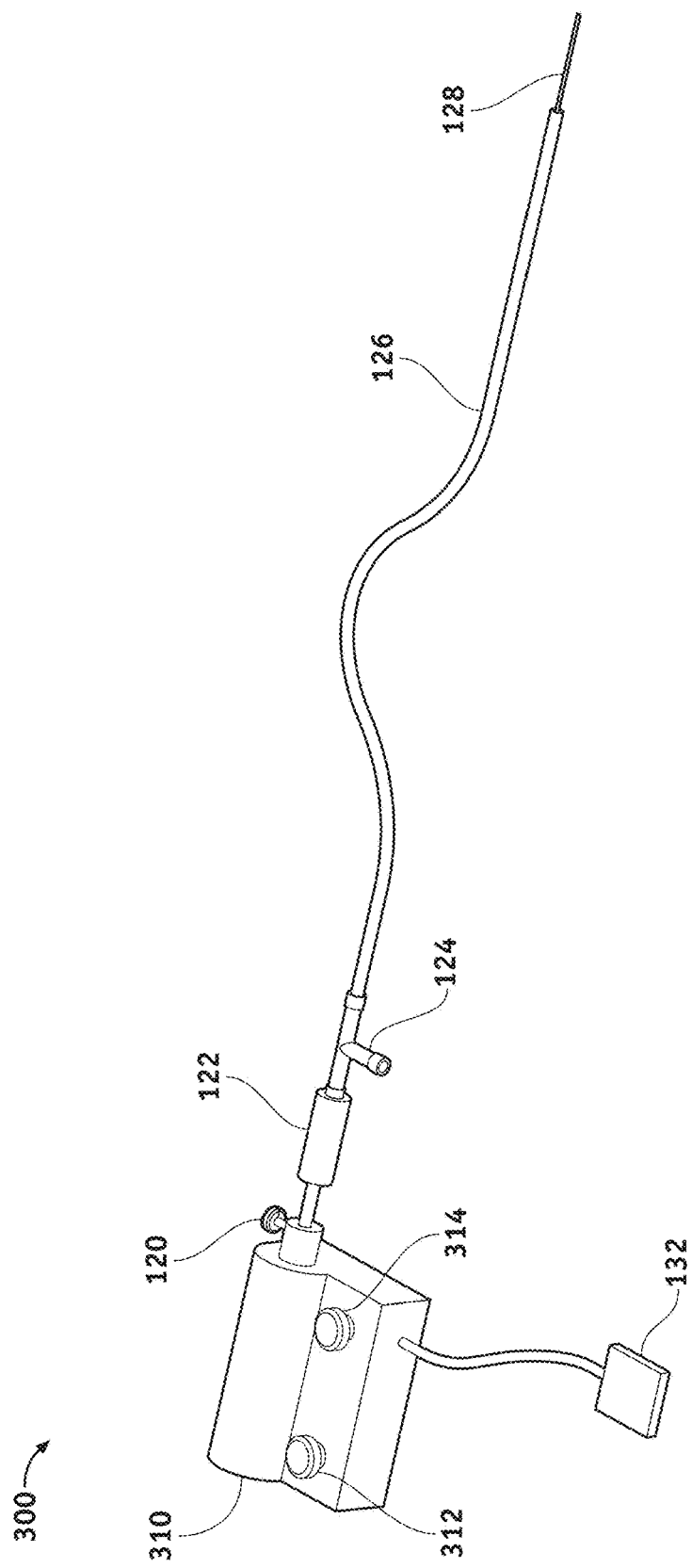
FIG. 3 depicts an example overview of a mountable arterial blockage drill in accordance with an embodiment of the disclosure.

In FIG. 3 a table mount example 300 is shown. A table mount example may reduce the fatigue of the surgeon from extended use. The driving components may be integrated into a table mount unit. In this example, the surgeon holds and articulates the guiding sleeve with the drilling wire by pushing the guidewire along the artery to open calcified plaques.

In this example the actuation components are contained in the mountable body 310. The drive electronics are controlled by controls 312 and 314 that control the amplitude of the percussive action as well as the RPM if a rotary actuator is utilized. The frequency of the piezoelectric actuator is maintained in resonance by either built in electronic hardware, control software or the like. A foot pedal switch 132 turns the arterial blockage percussive drill on and off, as needed, during the surgical procedure. The coarse length adjuster 120 and fine length adjuster 122 are coupled to the guiding sleeve. A fluid access port 124 allows fluids to be routed between the guiding sleeve 126 and the drilling wire 128.

Figure 4:
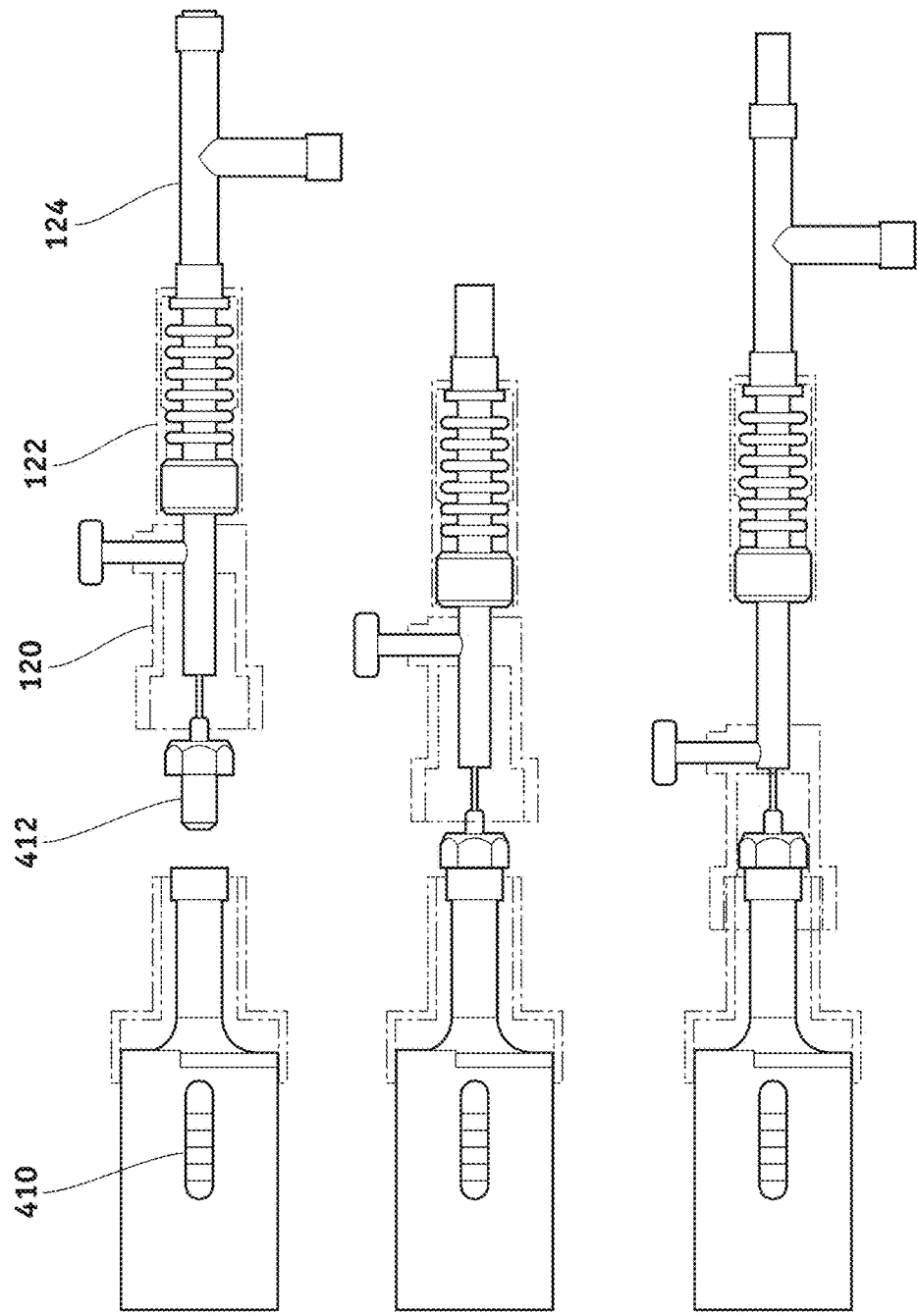
FIG. 4 depicts an example interfacing the drilling wire and guiding sleeve to the actuator assembly in accordance with an embodiment of the disclosure.

Arterial blockage percussive drill attachments and fixtures are shown in FIG. 4. To allow rapid replacement of guidewire, a coupler 412 to the actuator may be configured as shown in FIG. 1. The mounting of the guidewire and the attachments/fixtures is shown in FIG. 4. The drilling wire is inserted into the guiding sleeve that attaches to the motion transfer horn tip. Coarse length adjuster 120 and fine length adjusters 122 are used for coarse and fine adjustments of the guiding sleeve length prior to and during drilling, to exposure drilling wire inside the artery for penetrating occlusions. The coarse adjuster comprises a sleeve within a tube and a screw with a top knob allowing for clamping the two, once a length is set. A T shaped fluid access port 124 allows fluids to be routed between the guiding sleeve and the drilling wire to transport medications and saline for cooling the artery.

In FIG. 4 the arterial blockage percussive drill front end integration components comprise the components of interfacing the guidewire to the actuator 410. The guidewire is coupled to the motion transfer horn and the guiding sleeve interface components attach to the actuator coupling. The length adjusters and T shape fluid access port are shown.

The percussive actuator is comprised of at least two components, a piezoelectric element stack and a motion transfer horn that compresses the piezoelectric element stack to prevent damage to the piezoelectric element stack and to couple the output of the piezoelectric element stack to the drilling wire.

In most cases, due to the inherently low strain during excitation, piezoelectric materials are not used without amplifying their stroke. Even though generated stresses may be large, the stroke is generally on the order of nanometer or pico-meter displacements per volt. Additionally, the resonant frequency of a piezoelectric material is generally limited to the 100's of kHz, which is impractical for use in an arterial blockage percussive drill system. To address these potential limitations, a variety of actuator configurations may be used that involve the application of a piezoelectric multilayer stack kept under compression.

The coupling of a compressively stressed piezoelectric element stack to the drilling wire includes a motion transfer horn. Various examples of motion transfer horns will be shown and described. These percussive actuators have the capability to produce high force, high stroke and reasonable operating frequency range.

A first example of a percussive actuator comprising a piezoelectric element stack 510 and motion transfer horn 512 combination is the stepped horn percussive actuator shown in FIG. 5. The ultrasonic stepped horn percussive actuator amplifies plane waves and transmits large vibration energy to the drilling wire. This configuration allows operation at the ultrasonic frequency range of 20-60 kHz, which is beyond the hearing frequency range of most adults, making it quiet to the surgeon.

The stepped horn percussive actuator has an amplified displacement that is proportional to the mechanical quality factor (Qm) of the transducer and to the area ratio of the base to the motion transfer horn tip. If a strain wave is induced at the base of the motion transfer horn 512 at its resonance frequency, the displacement at the smaller end is amplified by a factor $M=(D1/D2)^2$ due to the conservation of the wave momentum. To prevent fracture of the piezoelectric stack 510 during operation a compression stress bolt is used. The induced vibrations are transferred to the drilling wire as percussive actuation. The stepped horn percussive actuator shown in FIG. 5 is a dog bone type and includes threads for attachment to a drilling wire.

Figure 6:
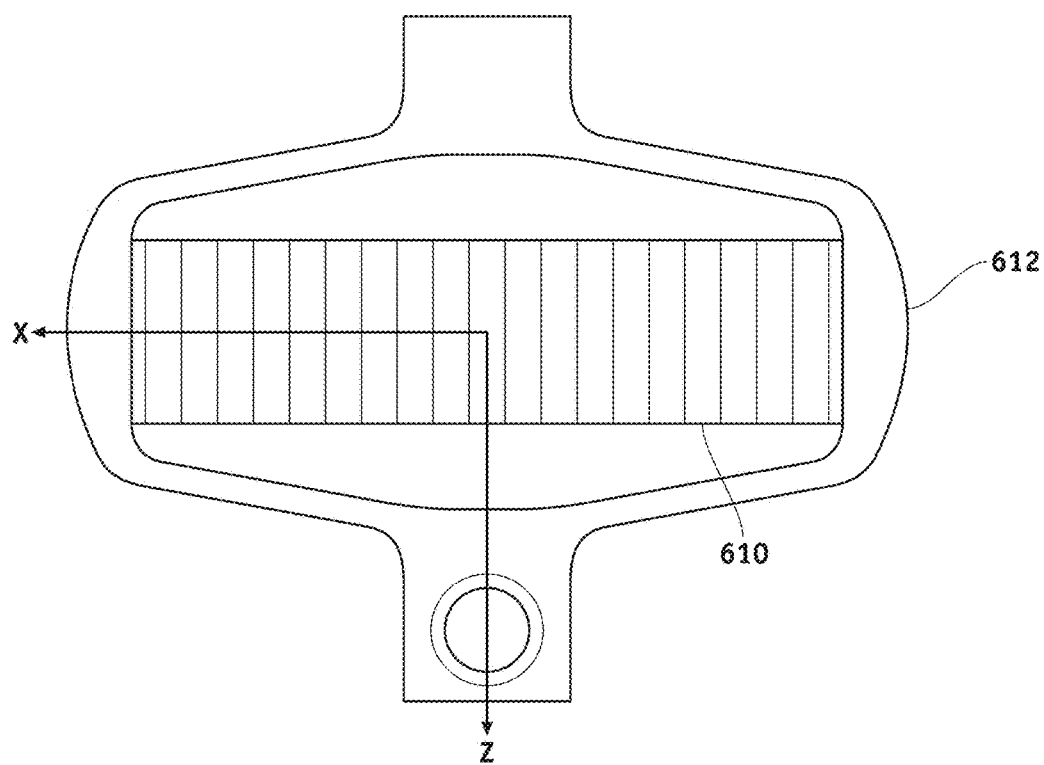
FIG. 6 depicts an example piezo transducer and flex tensional actuator in accordance with an embodiment of the disclosure.

A second type of percussive actuator is a flex tensional percussive actuator as shown in FIG. 6. The flex tensional percussive actuator couples a piezoelectric stack 610 to a flex tensional motion transfer horn 612 to produce a large stroke and a large force. The flex tensional percussive actuator is comprised of a multilayer stack of piezoelectric elements inside a metal frame. For a given applied voltage and fixed length, the effective piezoelectric strain coefficient of multilayer stacks is proportional to the number of the piezoelectric layers. Thus, using a stack with many layers of piezo material may generate the same displacement at much lower driving voltage.

The flex tensional percussive actuator schematic representation is shown in FIG. 6. The principle of operation is that a voltage applied to the piezoelectric stacks causes motion along the X axis that is the major axis, which in turn causes amplified motion along the Z axis that is the minor axis. The displacement amplification is related to the frame angle, i.e. the ratio of the long axis length (L) to the short axis height (h). The lower the angle of the actuator flexure with respect to the X axis, the higher the amplification. Under static conditions, the free strain of a piezoelectric element is typically 0.1% when driven at 150 V. In general, the displacement of flex tensional percussive actuator may be amplified from 1 to 20 times with an equivalent reduction of the blocked force.

Figure 7:
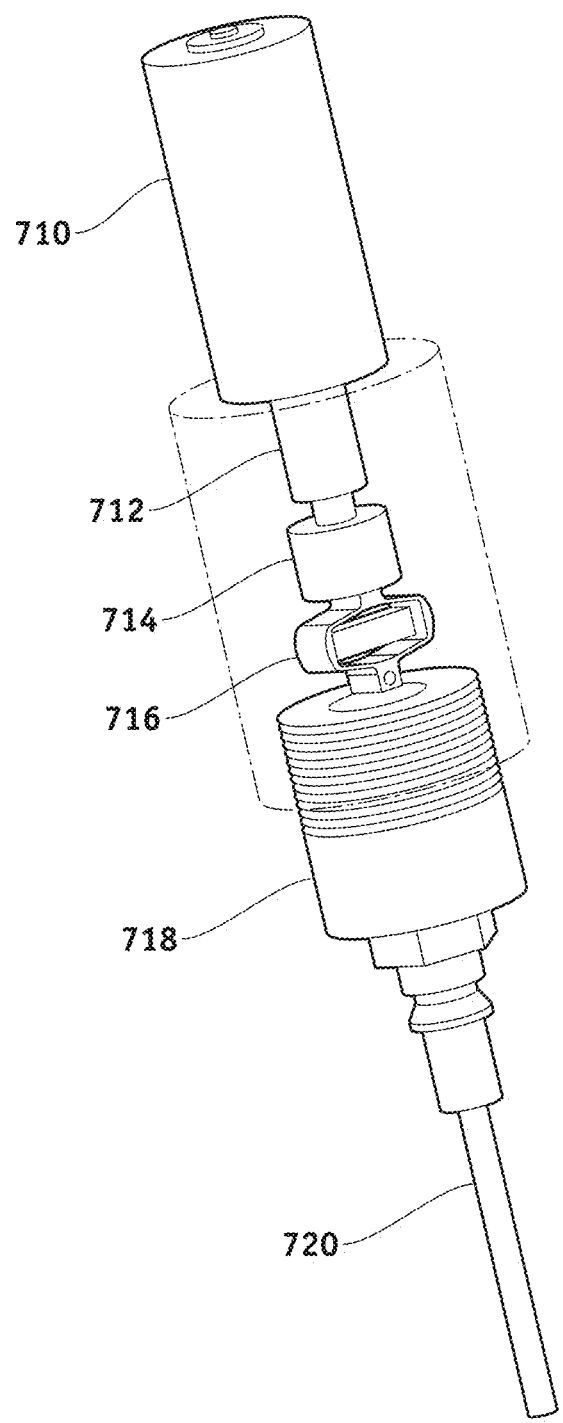
FIG. 7 depicts an example piezo transducer, flex tensional actuator and rotary electromagnetic actuator in accordance with an embodiment of the disclosure.

FIG. 7 depicts a flex tensional percussive actuator employed in the system. In this example an electromagnetic actuator 710 is coupled to a flexible coupling shaft 712 which is coupled to a slip ring 714 and to the flex tensional percussive actuator 716 described above. A chuck 718 is coupled to the guide wire assembly 720.

Figure 8:
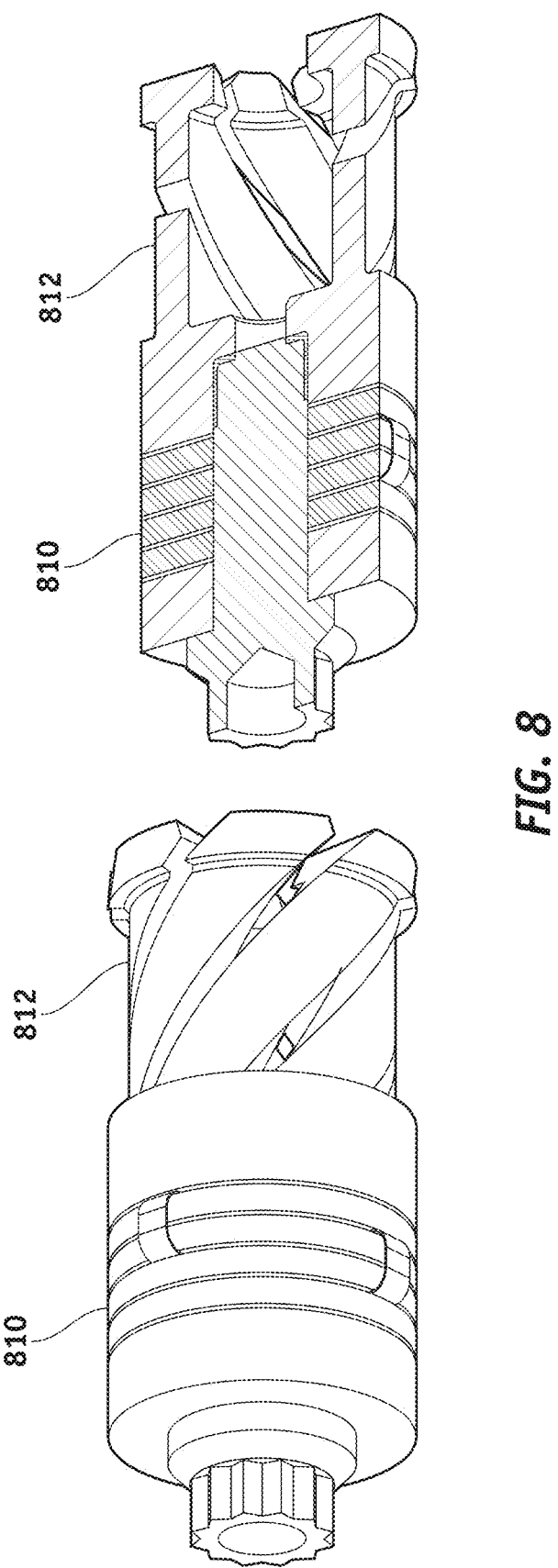
FIG. 8 depicts an example piezo transducer and longitudinal torsional actuator in accordance with an embodiment of the disclosure.
Figure 9:
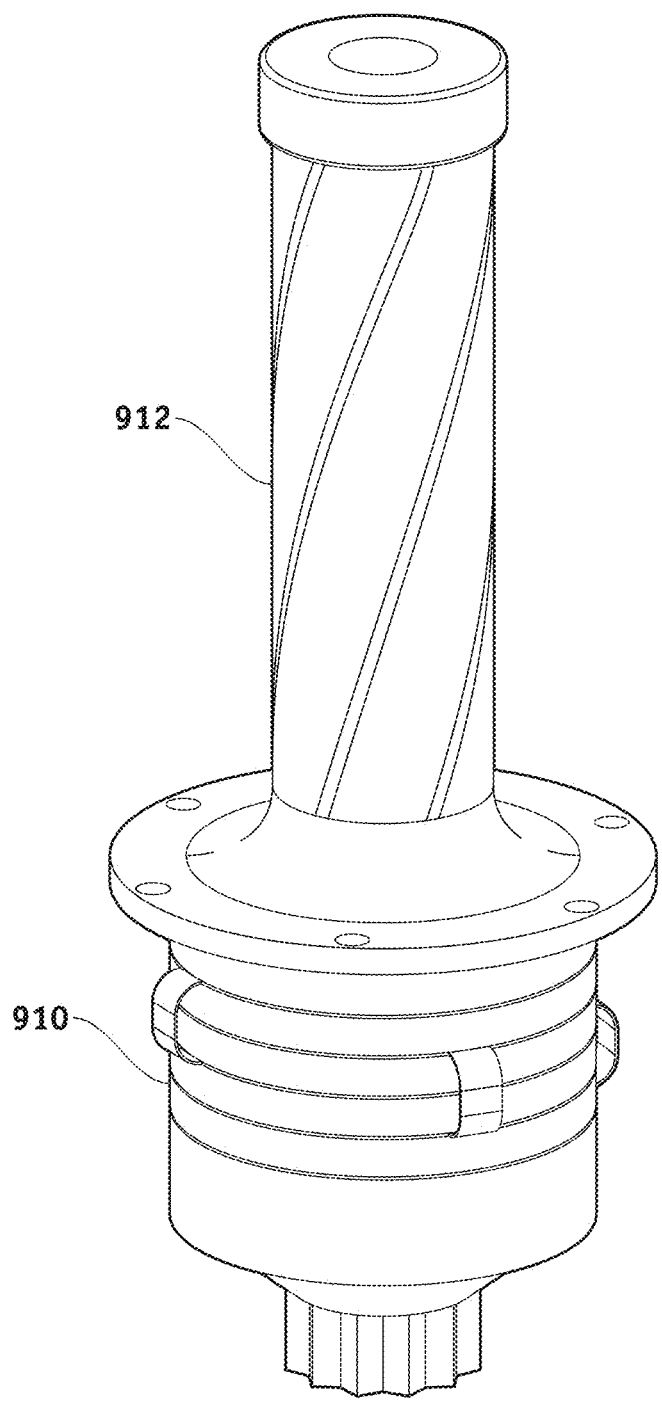
FIG. 9 depicts an example piezo transducer and longitudinal torsional actuator in accordance with an embodiment of the disclosure.

A third type of percussive actuator is shown in FIGS. 8 and 9 and is termed a longitudinal torsional percussive actuator. The longitudinal torsional percussive actuator converts the linear vibrations of the piezoelectric stack 810, 910 to a helical motion due to the longitudinal torsional motion transfer horn 812, 912.

Rotating and twisting the drilling wire during operation may be generated utilizing a single actuator coupled to a longitudinal torsional motion transfer horn. Apart from a longitudinal torsional motion transfer horn a complex mechanism with multiple parts may be used, this complex mechanism may increase the potential for failure of the mechanism. The longitudinal torsional percussive actuator simultaneously impacts and rotates the drilling wire in a helical motion.

The percussive impact action of the longitudinal torsional percussive actuator leads to penetration of the medium by producing a zone of finely crushed material directly ahead of the impacted location. This fracturing process is enhanced by shear forces from the ratcheting, rotation or twisting action. The shear motion due to rotation creates a ripping or chiseling action that increases the drilling efficiency and reducing the power. The rotation or twisting of the drilling wire may also minimize the risk of perforating the wall of the artery during the obstruction drilling process.

The longitudinal torsional percussive actuator comprises a piezoelectric stack 810, 910 that is compressed by a bolt between the backing and the motion transfer horn to prevent it from being subjected to tensile stress and potentially causing a failure. The backing is intended to transfer the generated mechanical vibrations towards the motion transfer horn. The motion transfer horn is configured asymmetrically with helical segments which imparts a helical action and upon impacting the drilling wire. This helical motion imparts longitudinal vibrations and tangential force causing both a percussive action and twisting action onto the drilling wire. The longitudinal component of the vibrations of the stack introduces percussion impulses between the drilling wire and the obstruction to fracture it when the ultimate strain of the obstruction is exceeded in the impact zone.

Figure 10:
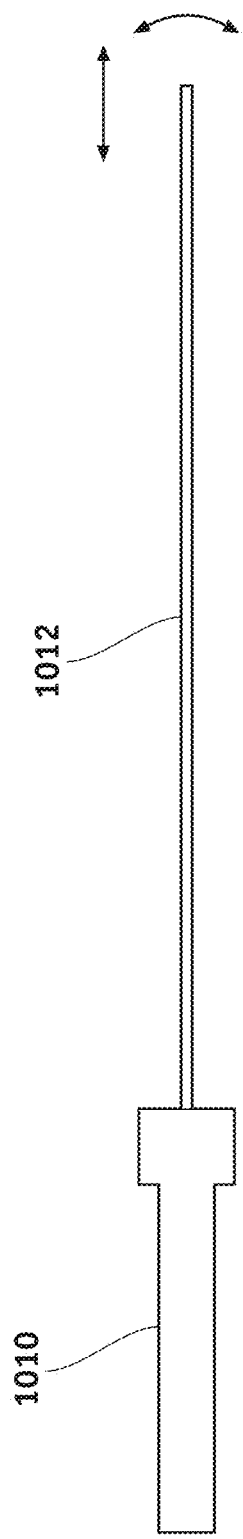
FIG. 10 depicts an example drilling wire directly coupled with a piezo transducer and longitudinal torsional actuator in accordance with an embodiment of the disclosure.
Figure 11:
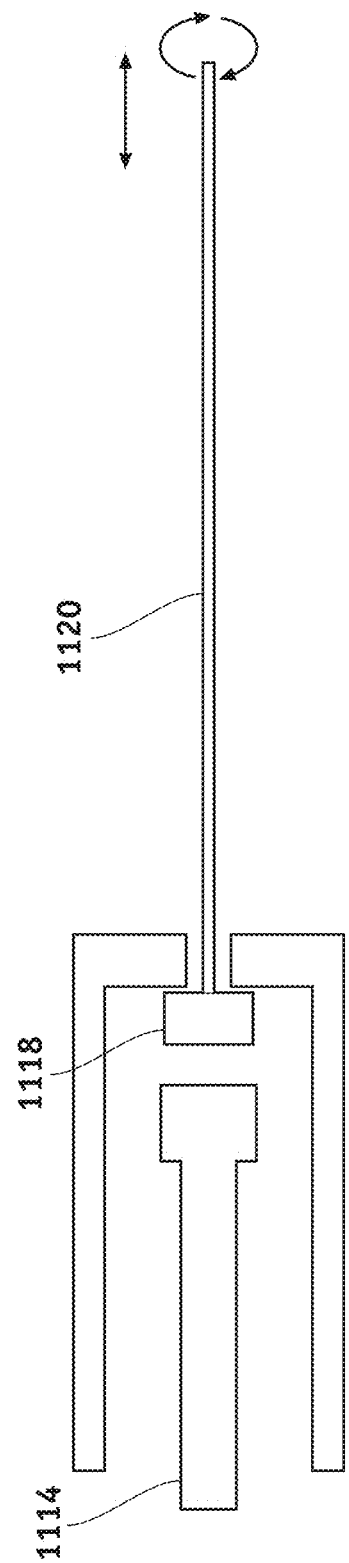
FIG. 11 depicts an example drilling wire frictionally coupled with a piezo transducer and longitudinal torsional actuator in accordance with an embodiment of the disclosure.
Figure 12:
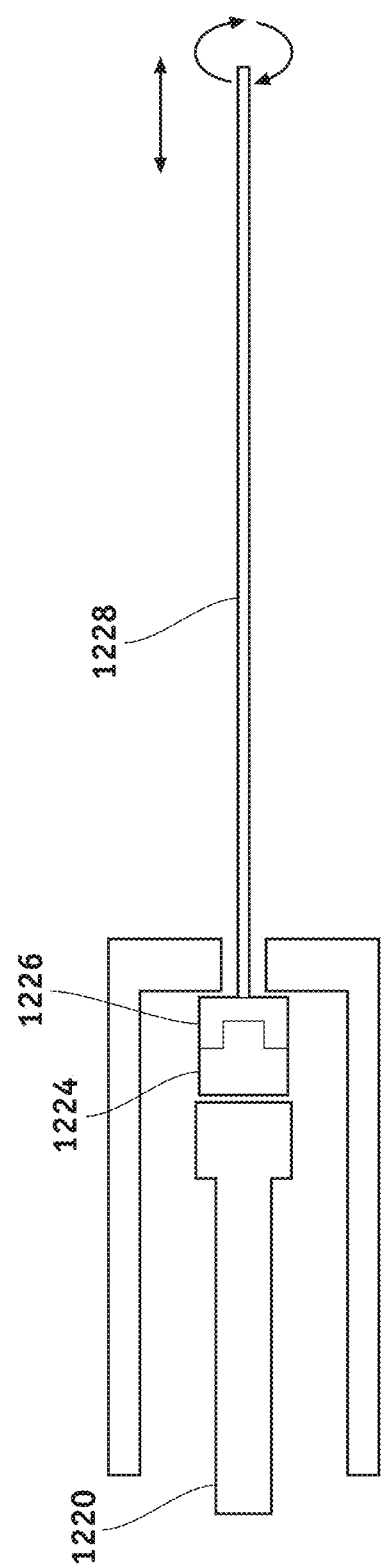
FIG. 12 depicts an example drilling wire key mass coupled with a piezo transducer and longitudinal torsional actuator in accordance with an embodiment of the disclosure.

FIGS. 10-12 illustrate three motion transfer horn to drilling wire coupling examples. FIG. 10 illustrates a solid connection between the motion transfer horn 1010 and the drilling wire 1012, in this solid connection the drilling wire may be screwed into the motion transfer horn or the drilling wire may be attached by chuck to the motion transfer horn. The configuration shown may be used where longitudinal and twisting of the drilling wire is utilized by firmly attaching the drilling wire to the motion transfer horn tip.

In FIG. 11 a free mass 1118 may be used to deliver hammering and twisting to the drilling wire 1120. To generate rotation the motion transfer horn tip 1114 drives a free mass 1118 which will vibrate longitudinally and spins due to the longitudinal and transverse impacts of the motion transfer horn tip on the free mass.

In FIG. 12 a keyed free mass 1224, 1226 may also be used to vibrate and transmit torque to the drilling wire 1228 from the motion transfer horn tip 1220.

A guidewire is the combination of a guiding sleeve and a drilling wire. The guide wire has a drilling end and an actuator end.

In one example a chuck may be used to couple the drilling wire to the percussive actuator. This allows the quick replacement of the guide wire while treating patients. The chuck has a drilling wire inserted into a hole with side clamps activated by springs, jaws, or using other bracing mechanisms. The fastening method may distribute the compressive forces and prevent fracture due to excessive stress concentration.

Figure 13:
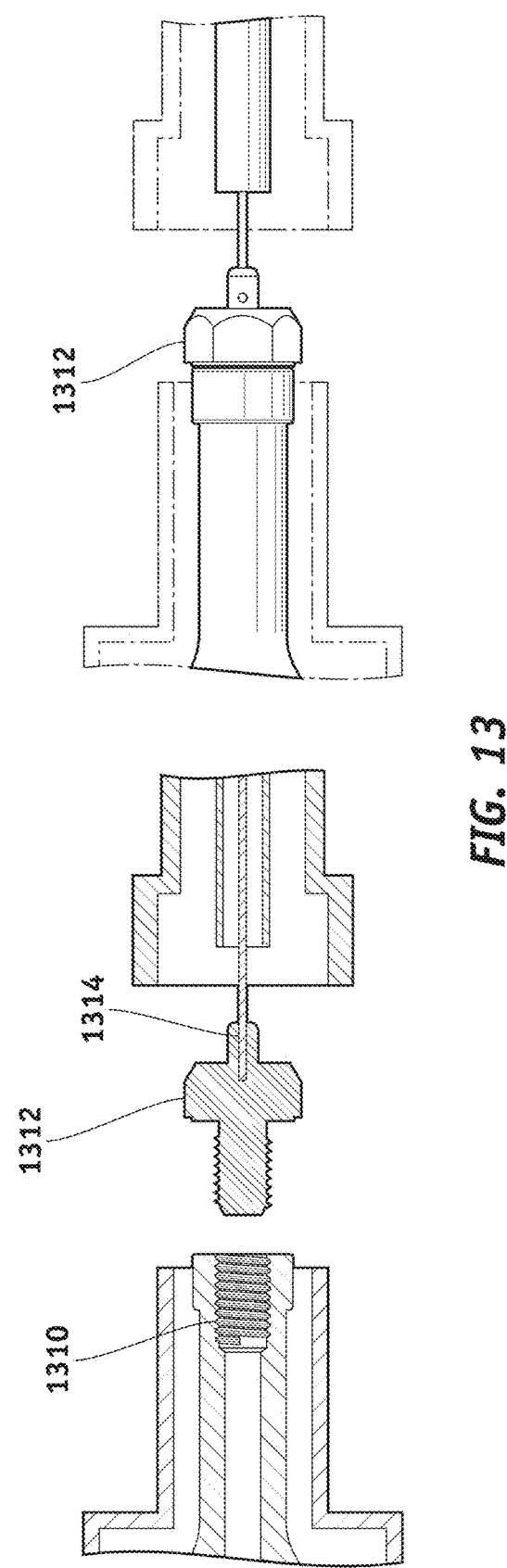
FIG. 13 depicts an example drilling wire threadably coupled to an actuator in accordance with an embodiment of the disclosure.

In one example shown in FIG. 13 the drilling wire 1314 may be coupled to the motion transfer horn of the actuator by brazing the wire to a threaded coupler 1312 which is screwed onto the motion transfer horn of 1310 the actuator. The drilling wire 1314 is seamed to the coupler by brazing or other joining methods. The brazing of the wire may be done at the outer end of the coupler.

Figure 14:
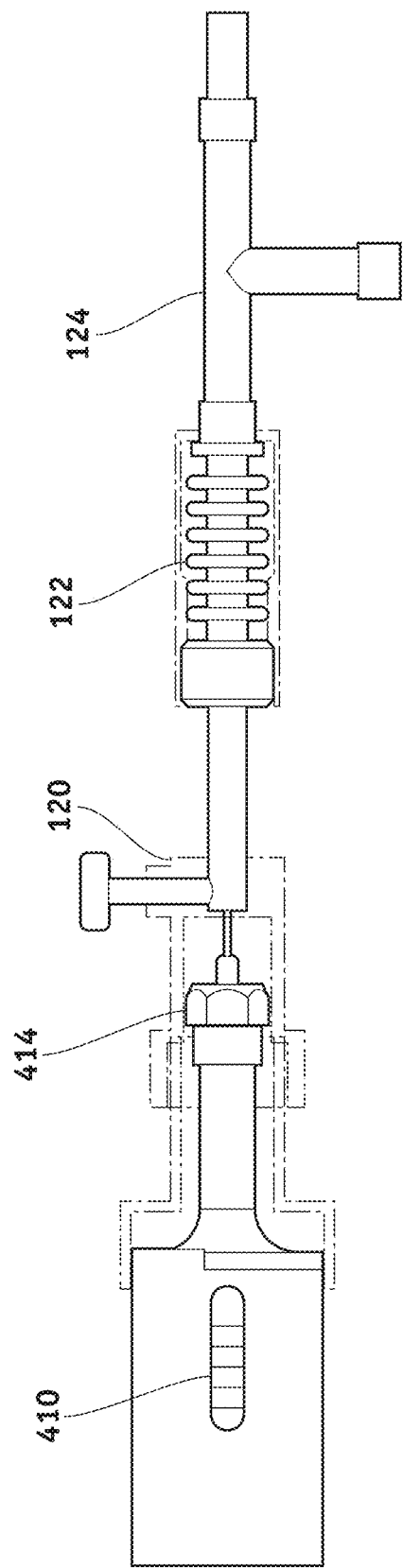
FIG. 14 depicts an example guide wire front end in accordance with an embodiment of the disclosure.

FIG. 14 depicts guide wire front end attachments such as a coarse length adjuster 120, a fine length adjuster 122 and a fluid access port 124 for injection of fluids such as saline that is used for cooling the drilling wire and may also include medication. The coupler 414 allows direction coupling of the drilling wire to the motion transfer horn 410.

Figure 16:
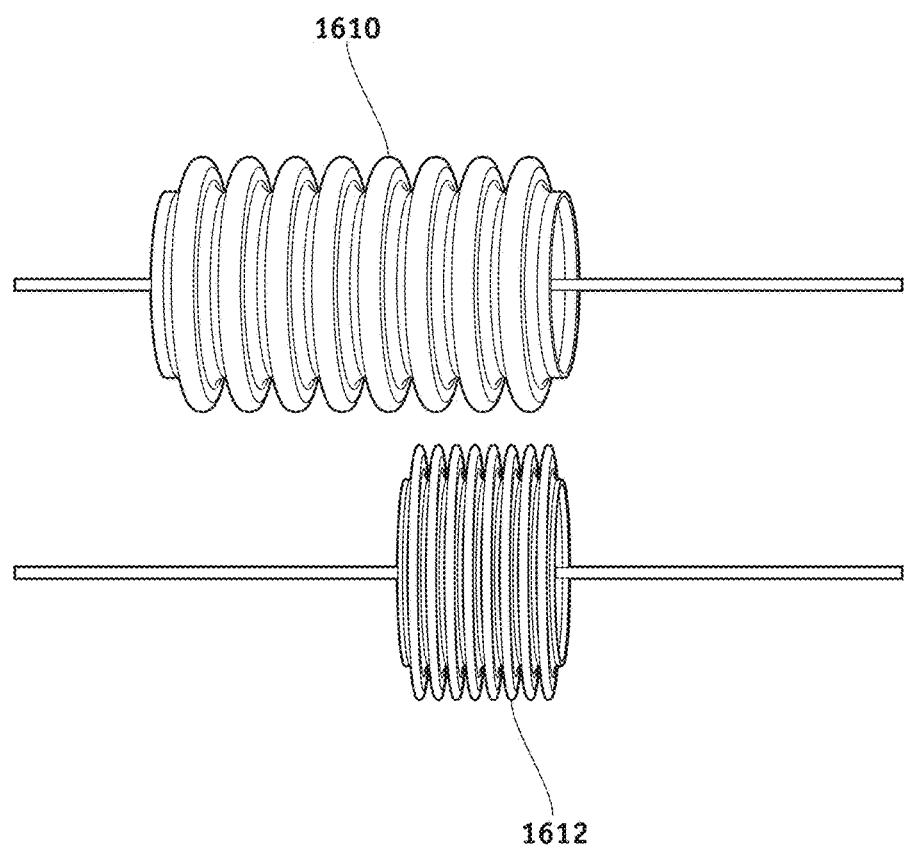
FIG. 16 depicts an example bellows fine length adjuster in accordance with an embodiment of the disclosure.
Figure 17:
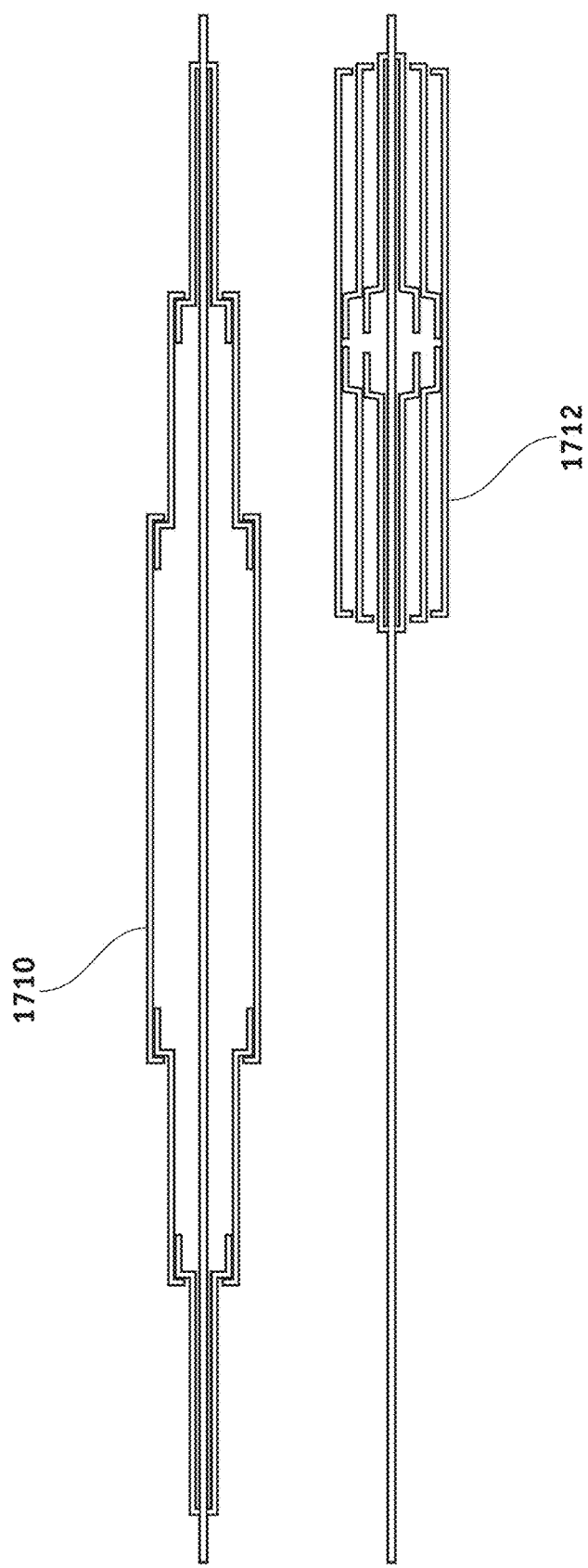
FIG. 17 depicts an example telescopic fine length adjuster in accordance with an embodiment of the disclosure in accordance with an embodiment of the disclosure.

Guiding sleeve length adjusters control the length of the drilling wire that is uncovered by the guiding sleeve to allow a wire length for penetrating the occlusion. The course adjuster comprises of a sleeve within a tube and the two are clamped at a predetermined length using a knob and a screw as shown in FIG. 15. The guiding sleeve is fully extended as shown by 1510, the coarse adjustment may allow full retraction of the guiding sleeve as shown by 1512 in which case the drilling wire extends from the end of the guiding sleeve by approximately the length of retraction of the guiding sleeve in this example. To allow adjusting the length during operation, while keeping the sleeve end as close to the occlusion surface as possible, a flexible fine adjuster is used that comprises a bellows, shown in FIG. 16 in expanded state 1610 and in compressed state 1612, telescopic, shown in FIG. 17 in extended state 1710 in retracted state 1712, or other such adjustable section.

As is shown in the example of FIG. 18, at the start of the operation 1810, the guiding sleeve is set to a maximum extended length. The extended length sets the maximum depth to be drilled through the occlusion. Upon reaching the minimal length of the adjuster, the drilling wire reaches the furthest distance 1816 that it may be pushed thru the occlusion. If additional drilling depth is sought, the coarse adjuster may be used.

The guiding sleeve guides the drilling wire to reach occlusions and protects the artery wall from being penetrated. The end of the sleeve is effectively the stopper that prevents the sleeve from further advance along the artery prior to the start of the occlusion drilling.

A schematic illustration of a penetrated occlusion is shown in FIG. 18. To maximize the protection of the blood vessel, the guiding sleeve is brought as close as possible to the occlusion surface. The tip of the drilling wire is kept at the end of the sleeve 1810 until the sleeve reaches the occlusion. Then, the guiding sleeve is retracted exposing the drilling wire which is pushed into the occlusion 1812, 1814, 1816 and impacts the occlusion as near the center of the occlusion as possible. The tip of the sleeve may also have a bullet shape that allows the sleeve to be passively guided along the artery.

Figure 19:
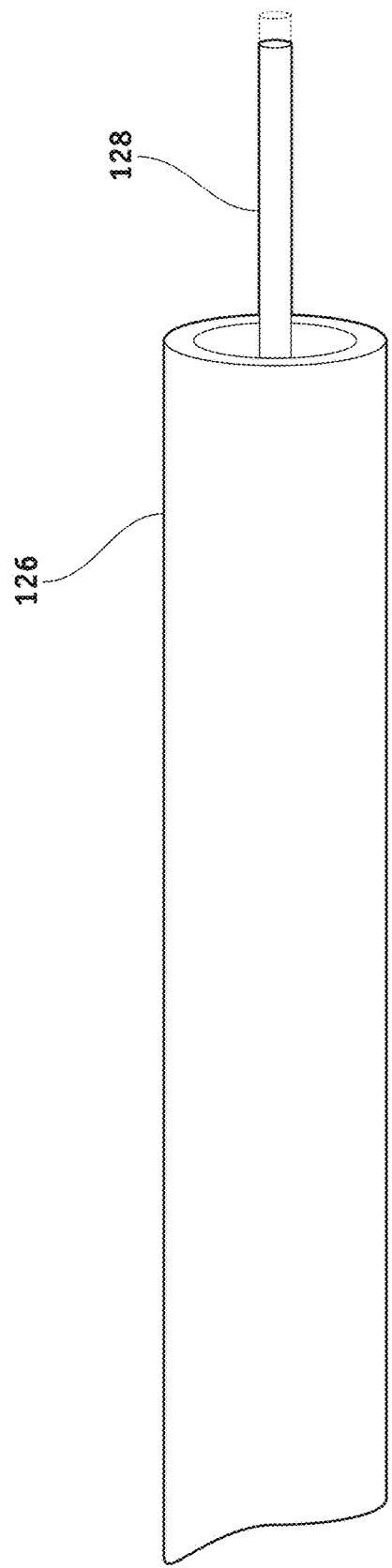
FIG. 19 depicts an example straight end guiding sleeve in accordance with an embodiment of the disclosure.

One example of a guiding sleeve with a straight cylindrical end having a tip of the drilling wire vibrating longitudinally is shown in FIG. 19. The direction and amplitude of the vibrations will depend on the drive frequency, the resonance and its harmonics and the driving voltage.

Figure 20:
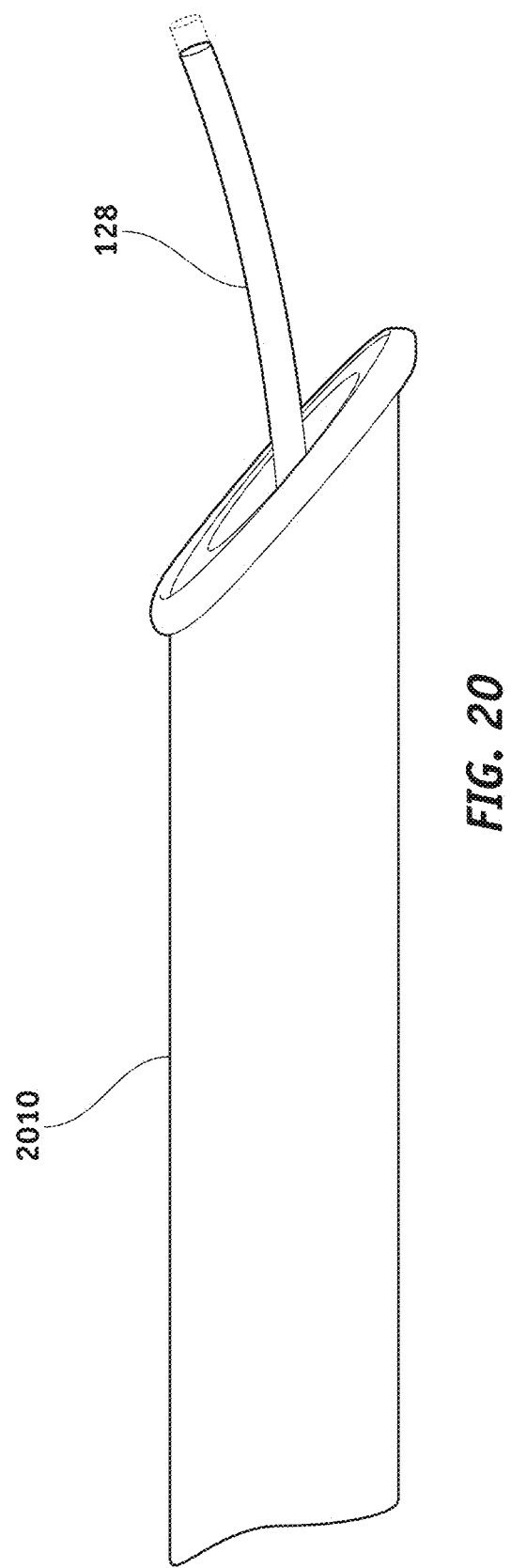
FIG. 20 depicts an example angulated end guiding sleeve in accordance with an embodiment of the disclosure.

The end of the guiding sleeve may have various angular configurations leading to asymmetric vibrations as shown in FIG. 20. The guiding sleeve 2010 may have an angulated end that may also be adjustable to center the tip of a drilling wire within the blood vessel and be flush with the surface of the occlusion. Thus, the guiding sleeve may include a small angle with bending ability while delivering the percussive vibrations. This configuration allows for transverse vibrations and by controlling the selected frequency the amplitude may be controlled while the direction of the movement is guided by the angle and orientation of the guiding sleeve end.

Figure 21:
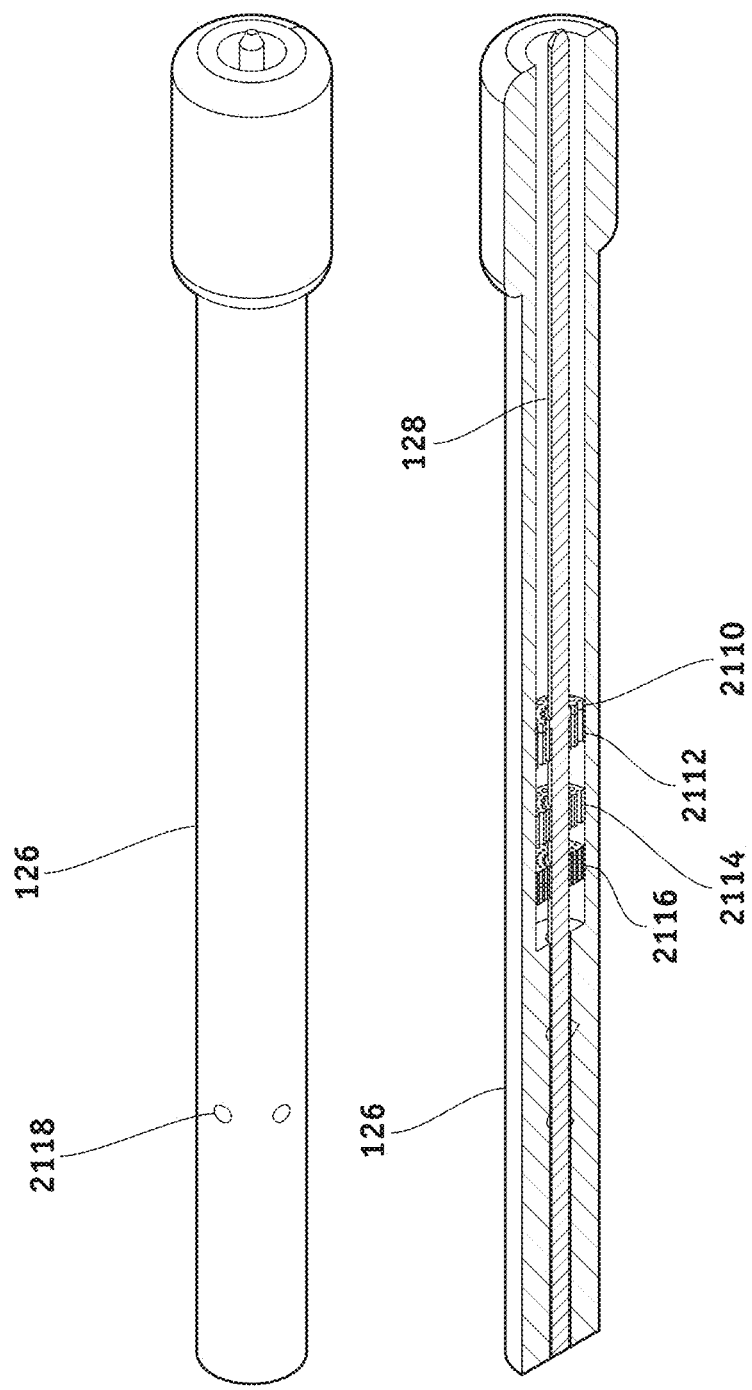
FIG. 21 depicts an example of a debris crusher prior to pushing the wire for drilling in accordance with an embodiment of the disclosure.
Figure 22:
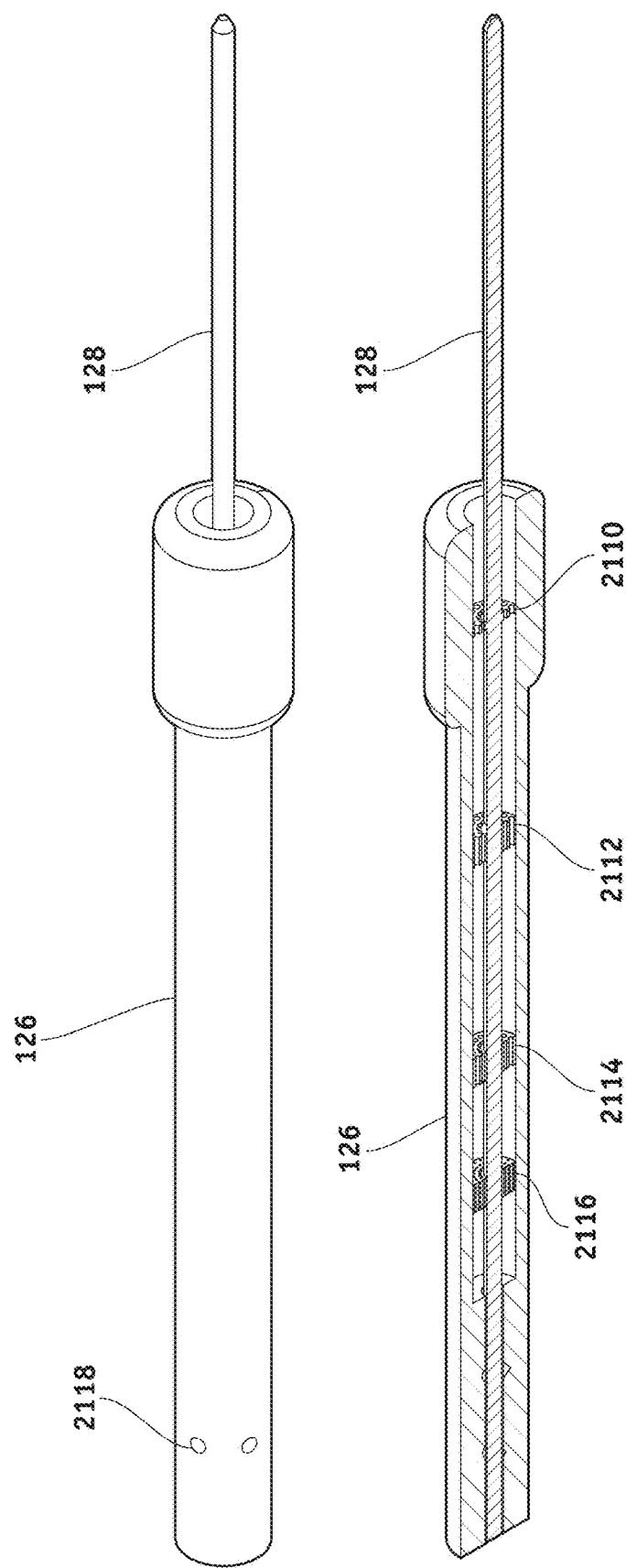
FIG. 22 depicts an example overview of a debris crusher after pushing the wire for drilling in accordance with an embodiment of the disclosure.
Figure 23:
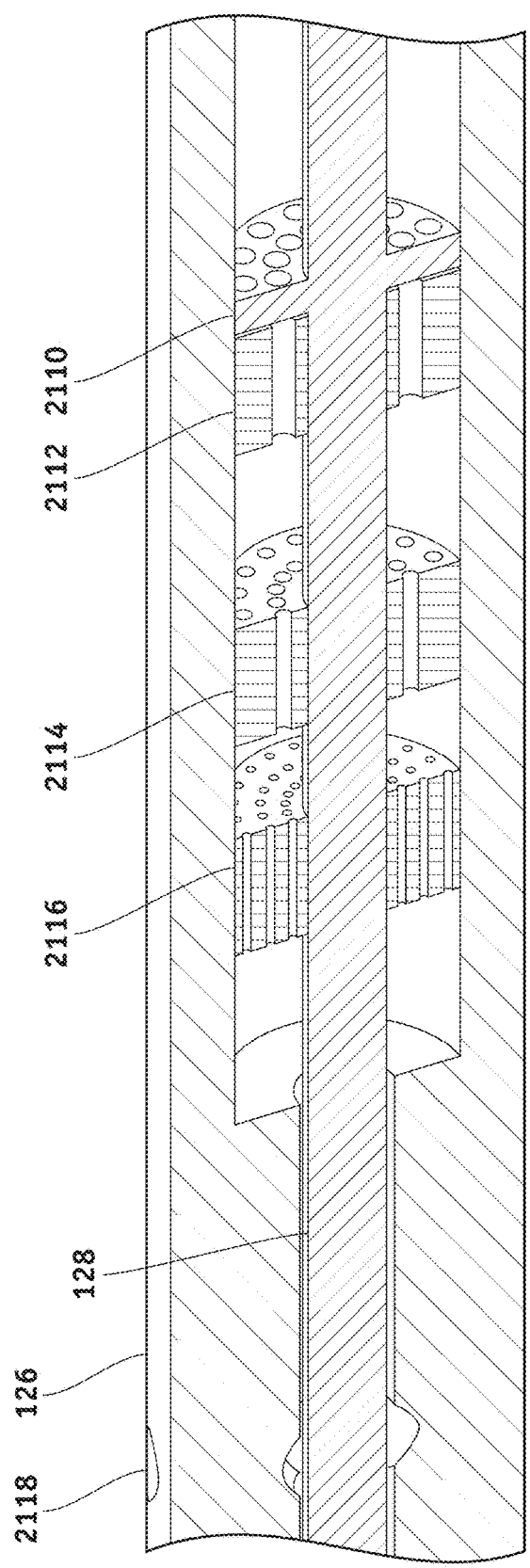
FIG. 23 depicts an example magnified view of a debris crusher during the vibratory action from the piezoelectric actuator in accordance with an embodiment of the disclosure.

FIGS. 21-23 depict a debris crusher and filter near the drilling wire end of the guiding sleeve. To assure that the size of the cutting particles is sufficiently small to prevent subsequent occlusions, a debris crusher crushes the particulates from the drilling process and larger debris fragments may be kept inside the guiding sleeve.

A schematic illustration of the debris crusher and filter inside the guiding sleeve are shown in FIG. 21. The components include a perforated hammer in the shape of a disc that acts like a crusher and comprises miniature perforated rods that crush the large particles and allow for the flow of blood during the vibratory penetration. Once the particulates are sufficiently reduced in size by perforated disk debris filters 2112, 2114 and 2116 they travel through the space between the drilling wire and the guiding sleeve and exit through vents 2118 in the guiding sleeve.

FIG. 21 depicts the guiding sleeve and drilling wire prior to retracting the guiding sleeve, i.e. prior to the drilling wire impacting the occlusion.

FIG. 22 depicts the guiding sleeve and the drilling wire after retracting the guiding sleeve for the drilling wire to contact the occlusion.

FIG. 23 is a close up of the perforated disk debris crusher 2110 for reducing efflux particulate size and the perforated disk debris filters 2112, 2114 and 2116 allowing blood flow. The perforated disk debris crusher 2110 moves back and forth during the vibratory action of the piezoelectric actuator, thus crushing the particulates between a perforated hammer and the first filter section.

Centering the guiding sleeve may be improved so as to place the end of the drilling wire directly on the occlusion by the inclusion of a guiding element such as cone, ball or the like that is smaller than 0.025 inch in diameter. This guiding element may be added just aft of the drilling wire tip thus leaving a portion of the drilling wire sticking out.

Figure 24:
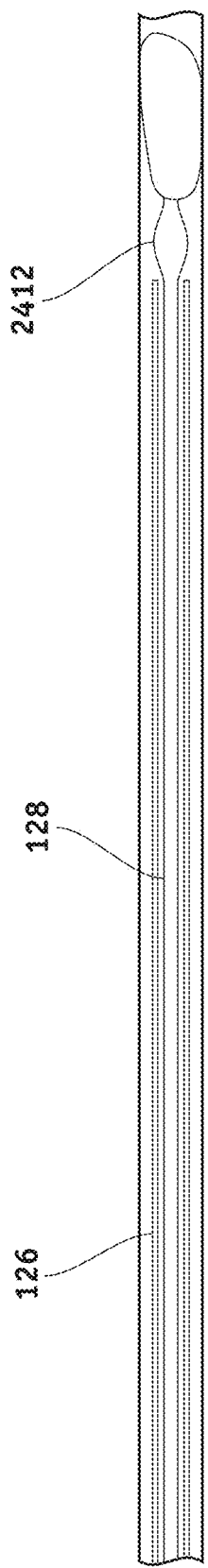
FIG. 24 depicts an example miniature guiding element in accordance with an embodiment of the disclosure.

FIG. 24 illustrates a guiding element 2412 that is coupled just aft of the end of the drilling wire 128. The guiding element 2412 may minimize the potential for having the wire pushed directly into the artery wall and thus increasing the safety of the surgical procedure.

EQUIVALENTS, EXTENSIONS, ALTERNATIVES AND MISCELLANEOUS

Example embodiments that relate to artery blockage drills are thus described. In the foregoing specification, embodiments of the present disclosure have been described with reference to numerous specific details that may vary from implementation to implementation. Thus, the sole and exclusive indicator of what may be the invention, and is intended by the applicants to be the invention, may be the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. An arterial blockage percussive drill, comprising:
   a vented guiding sleeve;
   a drilling wire slidably coupled to said vented guiding sleeve;
   a percussive actuator coupled to said drilling wire to longitudinally oscillate said drilling wire into an arterial blockage;
   a perforated disk debris crusher coupled to said drilling wire to crush debris drilled out by said drilling wire and oscillated by said percussive actuator; and
   a perforated disk debris filter coupled to said drilling wire to filter crushed debris and pass efflux to vents in said vented guiding sleeve.

2. The arterial blockage percussive drill of claim 1, further comprising a guiding sleeve retractor.

3. The arterial blockage percussive drill of claim 1, further comprising a guiding element coupled to said drilling wire to center said drilling wire in an artery.

4. The arterial blockage percussive drill of claim 1, further comprising a portable housing coupled to said percussive actuator.

5. The arterial blockage percussive drill of claim 1, further comprising a mountable housing coupled to said percussive actuator.

6. The arterial blockage percussive drill of claim 1, wherein said percussive actuator is piezoelectric.

7. The arterial blockage percussive drill of claim 1, further comprising a fluid access port coupled to said guiding sleeve to transport fluids to said drilling wire.

8. The arterial blockage percussive drill of claim 1, further comprising a controller to modulate a stroke of said percussive actuator.

9. The arterial blockage percussive drill of claim 1, wherein said percussive actuator is comprised of at least one of a stepped horn, a flextensional horn and a percussive rotary horn.

10. The arterial blockage percussive drill of claim 1, wherein said guiding sleeve is angularly articulable.

11. The arterial blockage percussive drill of claim 1, further comprising a rotary actuator coupled to said drilling wire to rotate said drilling wire.

12. The arterial blockage percussive drill of claim 11, wherein said rotary actuator oscillates said drilling wire.

13. The arterial blockage percussive drill of claim 11, wherein said rotary actuator rotates said drilling wire in one angular direction.

14. The arterial blockage percussive drill of claim 1, wherein said arterial blockage is a total occlusion.

* * * * *